(12) United States Patent
Yeung et al.

(10) Patent No.: US 8,445,497 B2
(45) Date of Patent: May 21, 2013

(54) COMPOUNDS FOR THE TREATMENT OF HEPATITIS C

(75) Inventors: Kap-Sun Yeung, Madison, CT (US); Brett R. Beno, Cromwell, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 169 days.

(21) Appl. No.: 13/167,356

(22) Filed: Jun. 23, 2011

(65) Prior Publication Data
US 2012/0165344 A1 Jun. 28, 2012

Related U.S. Application Data

(60) Provisional application No. 61/359,881, filed on Jun. 30, 2010.

(51) Int. Cl.
*A61K 31/496* (2006.01)
*C07D 239/26* (2006.01)

(52) U.S. Cl.
USPC .................................. 514/254.11; 544/294

(58) Field of Classification Search
USPC .................................. 514/254.11; 544/294
See application file for complete search history.

(56) References Cited

U.S. PATENT DOCUMENTS

| 7,265,152 | B2 | 9/2007 | Saha et al. |
|---|---|---|---|
| 7,868,037 | B2 | 1/2011 | Karp et al. |
| 7,994,171 | B2 | 8/2011 | Yeung et al. |
| 2009/0281336 | A1 | 11/2009 | Saha et al. |
| 2010/0063068 | A1 | 3/2010 | Pracitto et al. |
| 2010/0093694 | A1 | 4/2010 | Yeung et al. |

FOREIGN PATENT DOCUMENTS

| JP | 57-123181 | 7/1982 |
|---|---|---|
| WO | WO 02/16359 | 2/2002 |
| WO | WO 02/078701 | 10/2002 |
| WO | WO 2004/041201 | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |
| WO | WO 2011/103063 | 8/2011 |
| WO | WO 2011/106896 | 9/2011 |
| WO | WO 2011/106929 | 9/2011 |
| WO | WO 2011/106992 | 9/2011 |

OTHER PUBLICATIONS

U.S. Appl. No. 13/031,777, filed Feb. 22, 2011, Kadow et al.
U.S. Appl. No. 13/043,747, filed Mar. 9, 2011, Yeung et al.
Database Caplus [Online], Chemical Abstracts Service, Columbus, OH, US, Grinev, A.N. et al., "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.
Cheung, M., "The identification of pyrazolo[1,5-*a*]pyridines as potent p38 kinase inhibitors", Bioorganic & Medicinal Chemistry Letters, vol. 18, pp. 5428-5430 (2008).
Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).
Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).
Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).
Kakehi, A. et al., "Preparation of New Nitrogen-Bridged Heterocycles. XIV. Further Investigation of the Desulfurization and the Rearrangement of Pyrido[1,2-*d*]-1,3,4-thiadiazine Intermediates", Chem. Pharm. Bull., vol. 35, No. 1, pp. 156-169 (1987).
Miki, Y. et al., "Acid-Catalyzed Reactions of 3-(Hydroxymethyl)- and 3-(1-Hydroxyethyl)pyrazolo[1,5-*a*]pyridines", J. Heterocyclic Chem., vol. 26, pp. 1739-1745 (1989).

*Primary Examiner* — Taofiq A Solola
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

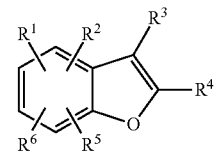

6 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/359,881 filed Jun. 30, 2010.

BACKGROUND OF THE INVENTION

The disclosure generally relates to the novel compounds of formula including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defraneesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during exteneded dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I,

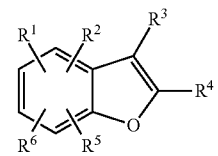

where:

$R^1$ is phenyl or pyridinyl and is substituted with 0-3 substituents selected from the group consisting of halo, alkyl, haloalkyl, hydroxyalkyl, alkoxyalkyl, alkoxy, hydroxyalkyloxy, and alkoxyalkyloxy, and is also substituted with 1 CON($R^9$)($R^{10}$) substituent;

$R^2$ is hydrogen, halo, or alkyl;

$R^3$ is CONHCH$_3$;

$R^4$ is phenyl that is para substituted with X—Ar$^1$;

$R^5$ and $R^6$ are independently hydrogen, alkyl, halo, N($R^7$)($R^8$), or alkylsulfonyl;

$R^7$ and $R^8$ are independently hydrogen, alkyl, hydroxyalkyl, alkoxyalkyl, alkylsulfonyl, or alkylsulfonylalkyl;

or N($R^7$)($R^8$) taken together is azetidinyl, pyrrolidinyl, piperidinyl, or piperazinyl, and is substituted with 0-2 substituents selected from alkyl, hydroxyalkyl, or hydroxy;

$R^9$ is hydrogen;

$R^{10}$ is

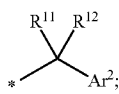

$R^{11}$ and $R^{12}$ are independently hydrogen, alkyl, hydroxyalkyl, or alkoxyalkyl;
or $R^{11}$ and $R^{12}$ taken together is ethylene, propylene, butylene, pentylene, or hexylene;
X is —O— or —NH—;
$Ar^1$ is phenyl or para-halophenyl; and
$Ar^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, or pyrimidinyl, and is substituted with 0-3 substituents selected from halo, alkyl, or dialkylamino;
or a pharmaceutically acceptable salt thereof.

Another aspect of the invention is a compound of formula I where
$R^1$ is phenyl substituted with 0-3 substituents selected from the group consisting of halo, alkyl, hydroxyalkyl, alkoxyalkyl, alkoxy, or hydroxyalkyloxy, and is also substituted with 1 $CON(R^9)(R^{10})$ substituent;
$R^2$ is hydrogen or F;
$R^3$ is $CONHCH_3$
$R^4$ is phenyl that is para substituted with $X$—$Ar^1$;
$R^5$ and $R^6$ are hydrogen;
$R^{11}$ and $R^{12}$ are independently methyl or $R^{11}$ and $R^{12}$ taken together is ethylene or propylene;
X is —O—;
$Ar^1$ is para fluorophenyl; and
$Ar^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, pyrimidinyl, and is substituted with 0-3 substituents selected from halo or alkyl;
or a pharmaceutically acceptable salt thereof.

Another aspect of the invention is a compound of formula I where $R^1$ is phenyl substituted with 1 $CON(R^9)(R^{10})$ 1 methyl substituent, and I methoxy substituent; $R^2$ is fluoro; $R^4$ is phenyl para substituted with $X$—$Ar^2$; $R^5$ and $R^6$ are hydrogen; $R^{10}$ is

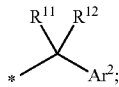

$R^{12}$ and $R^{13}$ taken together is ethylene; and $Ar^2$ is pyrimidinyl;
or a pharmaceutically acceptable salt thereof.

Another aspect of the invention is a compound of formula I where $R^1$ is phenyl substituted with 1 $CON(R^9)(R^{10})$ substituent and also substituted with 0-2 halo, alkyl, or alkoxy substituents.

Another aspect of the invention is a compound of formula I where $R^{10}$ is

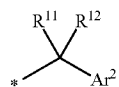

and $R^{12}$ and $R^{13}$ is ethylene or propylene.

Another aspect of the invention is a compound of formula I where $R^{10}$ is

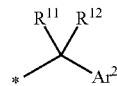

and $R^{12}$ and $R^{13}$ is ethylene.

Another aspect of the invention is a compound of formula I where $R^{10}$ is

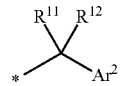

and at least one of $R^{12}$ and $R^{13}$ is not hydrogen.

Another aspect of the invention is a compound of formula I where $R^4$ is phenyl or monofluorophenyl.

Another aspect of the invention is a compound of formula I where $Ar^1$ is phenyl.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, X, $Ar^1$, or $Ar^2$ can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

Ethylene means ethanediyl or —$CH_2CH_2$—; propylene means propanediyl or —$CH_2CH_2CH_2$—; butylene means butanediyl or —$CH_2CH_2CH_2CH_2$—; pentylene means pentanediyl or —$CH_2CH_2CH_2CH_2CH_2$—.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

The compound demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM $MgCl_2$, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease T, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM $MgCl_2$, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. $^3$H-UTP was used at 0.6 μCi (029 μM total UTP). Reactions were initiated by the addition of enzyme, incubated at 30° C. for 60 min, and stopped by adding 25 μL of 50 mM EDTA containing SPA beads (4 μg/μL, Amersham RPNQ 0007). Plates were read on a Packard Top Count NXT after >1 hr incubation at room temperature.

Modified HCV NS5B RdRp enzyme assay. An on-bead solid phase homogeneous assay was also used to assess NS5B inhibitors (Wang Y-K, Rigat K, Roberts S, and Gao M (2006) Anal Biochem, 359: 106-111). The assay is a modification of the standard assay described above and was used in a 96-well or a 384-well format. The biotinylated oligo dT12 primer was captured on streptavidin-coupled beads (SPA beads (GE, RPNQ0007) or imaging beads (GE, RPNQ0261) by mixing primer and beads in buffer and incubating at room temperature for three hours. Unbound primer was removed after centrifitgation. The primer-bound beads were resuspended in 3× reaction buffer (40 mM Hepes buffer, pH 7.5, 7.5 mM $MgCl_2$, 7.5 mM KCl, dT primer coupled beads, poly A template, $^3$H-UTP, and RNAse inhibitor (Promega N2515). Compounds were serially diluted 1:3 in DMSO and aliquoted into assay plates. Equal volumes (20 μL for 96-well assay and 10 μl, for 384-well assay) of water, 3× reaction mix, and enzyme in 20 mM Hepes buffer, pH 7.5, 0.1 mg/ml BSA were added to the diluted compound on the assay plate. Final concentration of components in 96-well assay: 0.36 nM template, 15 nM primer, 0.43 μM (1 μCi) $^3$H-UTP, 0.08 U/μL RNAse inhibitor, 7 nM NS5B enzyme, 0.033 mg mL BSA, and 2 μg/μL beads, 20 mM Hepes buffer, pH 7.5, 2.5 mM $MgCl_2$, 2.5 mM KCl, 2% DMSO. Final concentration of components in 384-well assay: 0.2 mM template, 15 mM primer, 0.29 μM $^3$H-UTP (0.3 μCi), 0.08 U/μl RNAse inhibitor, 7 nM NS5B enzyme, 0.033 mg/mL BSA, and 0.33 μg/μL beads, 20 mM Hepes buffer, pH 7.5, 2.5 mM $MgCl_2$, 2.5 mM KCl, 2% DMSO.

Reactions were allowed to proceed for 4 hours at 30° C. and terminated by the addition of 50 mM EDTA (10 μL). After incubating for at least 15 minutes, plates were read on a Packard NXT Topcount or Amersham LEADseeker multimodality imaging system.

$IC_{50}$ values for compounds were determined using seven different [I]. $IC_{50}$ values were calculated from the inhibition using the formula y=A+((B−A)/(1+((C/x)^D))).

Cell lines. The cell lines used to evaluate compounds consist of a human hepatocyte derived cell line (Huh-7) that constitutively expresses a genotype 1a or 1b HCV replicon containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV replicon luciferase assay. To evaluate compound efficacy, HCV replicon cells were seeded in 96-well plates in DMEM containing 10% FBS at a cell density of $10^4$/well. Following incubation at 37° C. overnight, compounds serially diluted in DMSO were added to the cell plates. Alternatively, titrated compounds were transferred to sterile 384-well tissue-culture treated plates and the plates seeded with 50 µL of cells at a density of $2.4 \times 10^3$ cells/well in DMEM containing 4% FCS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a TopCount NXT Microplate Scintillation and Luminescence Counter (Packard) or Viewlux Imager (PerkinElmer) using a luminescence program. The 50% effective concentration ($EC_{50}$) was calculated using the exponential form of the median effect equation where $EC_{50}=100-[(\delta F_{inh}/\delta F_{con}) \times 100]$.

To assess cytotoxicity of compounds, Cell Titer-Blue (Promega) was added to the EnduRen-containing plates and incubated for at least 4 hrs at 37° C. The fluorescence signal from each well was read using a Cytoflour 400 (PE Biosystems) or Viewlux Imager. All $CC_{50}$ values were calculated using the median effect equation.

Representative data for a compound is reported iii Table 1.

TABLE 1

| Structure | $IC_{50}$ (µM) | $EC_{50}$ (µM) |
|---|---|---|
| | 24 | 5 | helper T cell response, interfering RNA, anti-sense RNA, Imigimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the Pharmaceutical Compositions and Methods of Treatment The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type I helper T cell response, interfering RNA, anti-sense RNA, Imigimod, ribavirin, an inosine 5'-monophospate dehydrogenase inhibitor, amantadine, and rimantadine.

HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |

TABLE 2-continued

| Brand Name | Type of Inhibitor or Target | Source Company |
|---|---|---|
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyeamide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxyberizotriazole hydrate; "DIEA" for diisopropylethylamine, "Nf" for $CF_3(CF_2)_3SO_2$—; and "TMOF" for trimethylorthoformate.

Ethyl 2-(4-bromophenyl)-5-hydroxybenzofuran-3-carboxylate was prepared according to the following scheme:

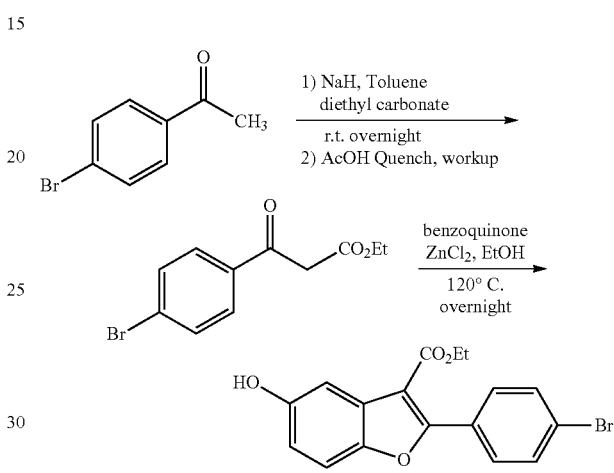

$^1$H NMR (400 MHz, DMSO-d$_6$) δ 9.50 (s, 1H), 7.91 (m, 2H), 7.74 (m, 2H), 7.50 (d, J=8.9 Hz, 1H), 7.37 (d, J=2.5 Hz, 1H), 6.86 (dd, J=8.9, 2.5 Hz, 1H), 4.32 (q, J=7.1 Hz, 2H), 1.32 (t, J=7.1 Hz, 3H). HPLC Method: SUNFIRE C18 (4.6×150) mm, 3.5 micron; Buffer: 0.05% TFA in water pH 2.5; Mobile Phase A: Buffer:MeCN (95:5); Mobile Phase B MeCN:Buffer (95:5); FLOW: 1 ml/min; Time: 0; B %: 10; Time: 12; B %: 100; Time: 15; B %: 100; Time: 18; B %: 10; Time: 23; B %: 10; Wavelength: 254 nm, RT min: 12.856; Wavelength: 220 nm, RT min: 12.856.

Ethyl 2-(4-bromophenyl)-4-fluoro-5-hydroxybenzofuran-3-carboxylate. To a mixture of ethyl 2-(4-bromophenyl)-5-hydroxybenzofuran-3-carboxylate (5 g, 13.84 mmol, 1.0 eq) in acetonitrile (300 ml) at r.t. was added selectfluor (6 g, 16.9 mmol, 1.22 eq) portion-wise, and the mixture stirred for 24 hr. After completion of reaction, the solvent was evaporated under vacuum. The residue was diluted with water, extracted with EtOAc (100 ml×3). The combined extracts were washed with saturated brine solution, dried over Na$_2$SO$_4$ and concentrated. The crude product was purified through silica gel (60-120 mesh) column using 10% EtOAc/Petroleum ether as eluent and further purified by preparative HPLC. Yield: 1.35 g (25.8%). $^1$H NMR (400 MHz, DMSO-d$_6$) δ 9.75 (s, 1H), 7.81-7.74 (m, 4H), 7.39 (d, J=8.4 Hz, 1H), 7.08 (t, J=8.4 Hz, 1H), 435-4.30 (q, J=6.8 Hz, 2H), 1.27 (t, J=6.8 Hz, 3H). Column: ZORBAX SB C18 (4.6×50 mm, 41m); Mobile phase A: 10% MeOH-90% H$_2$O-0.1% TFA; Mobile phase B: 90% MeOH-10% H$_2$O-0.1% TFA; Flow: lML/min; Time: 0; % A: 100; % B: 0; Time: 2; % A: 0; % B: 100; Retention Time min: 2.137, wavelength: 220 nm. PREPARATIVE HPLC METHOD Column: Symmetry C18(250×4.6)5µ; Mobile Phase A: 0.05% TFA in Water (15); Mobile Phase B: MeOH (85); FLOW: 1 ml/min; RT: 9.33 min.

4-Fluoro-2-(4-bromophenyl)-5-hydroxybenzofuran-3-carboxylic acid. To a mixture of ethyl 4-fluoro-2-(4-fluorophenyl)-5-hydroxybenzofuran-3-carboxylate (0.75 g, 1.97 mmol, 1.0 eq) in a 1:1 mixture of MeOH/THF at r.t. was added 1M aqueous NaOH solution (0.35 g, 8.75 mmol, 4.4 eq), and the mixture heated to 60° C. for 4 h.

The mixture was then cooled to r.t., concentrated, diluted with water and acidified with 1.5 N HCl. The solid was filtered, washed with water and dried in vacuum. Yield: 0.62 g (89.3%)

$^1$H NMR (400 MHz, DMSO-$d_6$) δ 13.38 (bs, 1H), 9.70 (s, 1H), 7.83-7.75 (m, 4H), 7.37 (d, J=8.0 Hz, 1H), 7.07 (t, J=8 Hz, 1H). Column: purospher@star RP-18 (4×55) mm, 3 µm; Mphase A: 20 mM NH$_4$OAc in 90% H$_2$O, 10% MeCN; Mphase B: 20 mM NH$_4$OAc in 10% H$_2$O, 90% MeCN; Flow: 2.5 mL/min; Time: 0; % A: 100; % B: 0; Time: 2; % A: 0; % B: 100; RT min: 1.23, wavelength: 220 nm.

4-Fluoro-2-(4-bromophenyl)-5-hydroxy-N-methylbenzofuran-3-carboxamide. To a mixture of 4-fluoro-2-(4-bromophenyl)-5-hydroxybenzofuran-3-carboxylic acid (0.62 g, 1.77=10, 1 eq), 2M solution of methylamine in THF (5.4 ml, 10.8 mmol, 6.1 eq), HOBT (0.43 g, 3.18 mmol, 1.8 eq), EDCI.HCl (0.61 g, 3.18 mmol, 1.8 eq) in THF at r.t. under an nitrogen atmosphere was added diisopropylethylamine (1.9 ml, 10.9 mmol, 6.2 eq). The clear reaction mixture was stirred at r.t. overnight. The reaction mixture was concentrated and diluted with water, and then the solid precipitate was collected by filtration. The product was washed with petroleum ether and dried under vacuum. Yield: 0.51 g (79.7%). $^1$H NMR (400 MHz, DMSO-$d_6$) δ 9.67 (s, 1H), 8.63 (t, J=4.4 Hz, 1H), 7.79-7.72 (m, 4H), 7.33 (d, J=8.8 Hz, 1H), 7.02 (m, 1H), 2.81 (d, J=4.4 Hz, 3H).

Column: purospher@star RP-18 (4×55) mm, 3 µm; Mphase A: 20 mM NH$_4$OAc IN 90% H$_2$O, 10% MeCN; Mphase B 20 mM NH$_4$OAc IN 10% H$_2$O, 90% MeCN; Flow: 2.5 mL/min; Time: 0; % A: 100; % B: 0; Time: 2; % A: 0;% B: 100; RT min: 1.704, wavelength: 220 nm.

4-Fluoro-2-(4-bromophenyl)-5-isopropoxy-N-methylbenzofuran-3-carboxamide. To a mixture of 4-fluoro-2-(4-bromophenyl)-5-hydroxy-N-methylbenzofuran-3-carboxamide (0.17 g, 0.467 mmol, 1 eq), 2-bromopropane (0.18 ml, 1.46 mmol, 3.1 eq), and cesium carbonate (0.46 g, 1.41 mmol, 3 eq) in N-methylpyrrolidinone in a sealed tube was heated at 50° C. for 16 h. The reaction mixture was cooled to r.t., and the inorganic was removed by filtration. The filtrate was diluted with water, and the product extracted into EtOAc. The organic was washed with saturated brine solution, filtered, dried over Na$_2$SO$_4$ and concentrated. The crude product was purified by silica gel (60-120) column chromatography using 0-20% EtOAc in petroleum ether as an eluent Yield: 0.15 g (79.4%). $^1$H NMR (400 MHz, DMSO-$d_6$) δ 8.66 (d, J=4.4 Hz, 1H), 7.78-7.73 (m, 4H), 7.46 (d, J=9.2 Hz, 1H), 7.26 (t, J=8.4 Hz, 1H), 4.53 (m, 1H), 2.82 (d, J=4.4 Hz, 3H). 1.29 (d, J=6.0 Hz, 6H). Column: purospher@star RP-18 (4×55) mm, 3 µm; Mphase A: 20 mM NH$_4$OAc in 90% H$_2$O, 10% MeCN; Mphase B: 20 mM NH$_4$OAc in 10% H$_2$O, 90% MeCN; Flow: 2.5 ML/min; Time: 0; % A: 100; % B: 0; Time: 1.8; % A: 0; % B: 100; RT min: 2.117, wavelength: 220 nm.

4-Fluoro-2-(4-(4-fluorophenoxy)phenyl)-5-isopropoxy-N-methylbenzofuran-3-carboxamide. A mixture of 4-fluoro-2-(4-bromophenyl)-5-isopropoxy-N-methylbenzofuran-3-carboxamide (0.15 g, 0.37 mmol, 1 eq), 4-fluorophenol (0.225 g, 2.0 mmol, 5.4 eq), Pd(OAc)$_2$ (5 mg, 0.02 mmol, 0.06 eq), X-phos (16 mg, 0.037 mmol, 0.1 eq) and K$_3$PO$_4$ (0.2 g, 0.94 mmol, 2.5 eq) in toluene in sealed tube was purged with N$_2$ gas for 5 minutes, and the reaction mixture heated at 50° C. for 16 h. The reaction mixture was cooled to r.t., and the inorganic was removed by filtration. The filtrate was diluted with water and extracted with EtOAc. The organic was washed with a saturated brine solution, dried over Na$_2$SO$_4$ and concentrated. The crude product was purified by silica gel (60-120) column chromatography using 0-20% EtOAc in petroleum ether as eluent. Yield: 0.12 g (75.0%). $^1$H NMR (400 MHz, DMSO-$d_6$) δ 8.64 (d, J=4.8 Hz, 1H), 7.85 (d, J=8.8 Hz, 2H), 7.44 (d, J=8.8 Hz, 1H), 7.31-7.27 (m, 2H), 7.24-7.17 (m, 3H), 7.12 (d, J=9.2 Hz, 2H), 4.53 (m, 1H), 2.81 (d, J=4.4 Hz, 3H), 1.30 (d, J=6 Hz, 6H).

LCMS: (ES+) m/z=438.2 (M+H)$^+$; Column: Xbridge phe (4.6×30 mm-3.5 µm); Mphase A: 2% MeCN in 98% H$_2$O-10 mM NH$_4$COOH; Mphase B 98% MeCN in 2% H$_2$O-10 mM NH$_4$COOH; Flow: 1.8 mL/min; Time: 0; % A: 100; % B: 0; Time: 1.5; % A: 0; % B: 100; RT min: 1.85, wavelength: 220 nm.

4-Fluoro-2-(4-(4-fluorophenoxy)phenyl)-5-hydroxy-N-methylbenzo-furan-3-carboxamide. To a mixture of 4-fluoro-2-(4-(4-fluorophenoxy)phenyl)-5-isopropoxy-N-methyl-benzofuran-3-carboxamide (0.12 g, 0.27 mmol, 1 eq) in CH$_2$Cl$_2$ was added BCl$_3$ (5 ml, 5.0 mmol, 18.5 eq, 1M in toluene). The reaction mixture was stirred at r.t. for 3 h, and then the reaction quenched with a saturated solution of NaHCO$_3$. The mixture was diluted with water, and the product extracted into CH$_2$Cl$_2$. The organic was washed with a saturated brine solution, dried over Na$_2$SO$_4$ and concentrated. Yield: 0.1 g (92.0%). $^1$H NMR (400 MHz, CD$_3$OD) δ 7.85 (d, J=2 Hz, 2H), 7.83-7.05 (m, 7H), 6.97 (d, J=8.2 Hz, 1H), 2.96 (d, J=4 Hz, 3H). LCMS: (ES–) m/z=394.0 (M–H); Column: Xbridge phe (4.6×30 mm-3.5 µm); Mphase A 2% MeCN in 98% H$_2$O-10 mM NH$_4$COOH; Mphase B 98% MeCN in 2% H$_2$O-10 mM NH$_4$COOH; Flow: 1.8 mL/Min; Time: 0; % A: 100; % B: 0; Time: 1.5; % A: 0; % B: 100; RT min: 1.667, wavelength: 220 nm.

4-Fluoro-2-(4-(4-(4-fluorophenoxy)phenyl)-3-(methylcarbamoyl)benzofuran-5-yl trifluoromethanesulfonate. To a solution of 4-fluoro-2-(4-(4-fluorophenoxy)phenyl)-5-hydroxy-N-methylbenzofuran-3-carboxamide (0.1 g, 0.25 mmol, 1.0 eq) in CH$_2$Cl$_2$ at r.t. under N$_2$ was added triethylamine (0.1 ml, 0.71 mmol, 2.8 eq). The mixture was cooled to 0° C. and added with N-phenyl-bis-(trifluoromethane sulfonamide) (0.11 g, 0.31 mmol, 1.2 eq), and then stirred at r.t. for 3 hr. The reaction mixture was concentrated under vacuum, and the residue diluted with water and then extracted with CH$_2$Cl$_2$. the organic layer was washed with a saturated brine solution, dried over Na$_2$SO$_4$ and concentrated. The crude product was purified by silica gel (60-120) column chromatography using 0-10% EtOAc in petroleum ether as an eluent to get the desired product as an off white solid. Yield: 0.126 g (94.7%). $^1$H NMR (400 MHz, DMSO-$d_6$) δ 8.77 (d, J=4.4 Hz, 1H), 7.89-7.86 (m, 2H), 7.75-7.65 (m, 2H), 7.33-7.28 (m, 2H), 7.23-7.15 (m, 4H), 2.84 (d, J=4.8 Hz, 3H). LCMS: (ES+) m/z=528.0 (M+H)$^+$; Column: Xbridge phe (4.6×30 mm-3 µm); Mphase A: 2% MeCN in 98% H$_2$O-10 mM NH$_4$COOH; M phase B 98% MeCN in 2% H$_2$O-10 mM NH$_4$COOH; Flow: 1.8 mL/min; Time: 0; % A: 100; % B: 0; Time: 1.5; % A: 0; % B: 100; RT min: 1.89, wavelength: 220 nm.

Methyl 5-(4-fluoro-2-(4-(4-fluorophenoxy)phenyl)-3-(methylcarbamoyl)benzofuran-5-yl)-2-methoxy-4-methylbenzoate. To a mixture of 4-fluoro-2-(4-(4-fluorophenoxy)phenyl)-3-(methylcarbamoyl)benzofuran-5-yl trifluoromethanesulfonate (0.11 g, 0.208 mmol, 1 eq), methyl 2-methoxy-4-methyl-5-(4,4,5,5-tetramethyl-1,3,2-dioxaborolan-2-yl)benzoate (0.075 g, 0.245 mmol, 1.18 eq) in toluene/EtOH (4:1) was added 1.0 M aqueous Na$_2$CO$_3$ (0.09 g, 0.849 mmol, 4.0 eq), and the mixture was purged with N$_2$ for 10 min. Tetrakis(triphenylphosphine) palladium(0) (0.022 g, 0.019 mmol, 0.09 eq) was added, and again $N_2$ was purged through the reaction mixture for 10 min. The above reaction mixture was heated at 100° C. overnight. The toluene layer was separated, and the aqueous layer extracted with EtOAc. The organic layers were combined and concentrated. The product obtained was purified by silica gel (60-120) column chromatography using 40% EtOAc/Hexane as eluent. Yield: 94 mg (77.6%). $^1$H NMR (400 MHz, DMSO-$d_6$) δ 8.67 (d, J=4.4 Hz, 1H), 7.89 (d, J=8 Hz, 2H), 7.60 (d, J=6.4 Hz, 1H), 7.53 (s, 1H), 7.32-7.26 (m, 3H), 7.21-7.14 (m, 3H), 7.14 (d, J=6.8 Hz, 2H), 3.88 (s, 3H), 3.77 (s, 3H), 2.79 (d, J=4.8 Hz, 3H), 2.21 (s, 3H).

LCMS: (ES+) m/z=558.2 (M+H)$^+$. Column: Xbridge phe (4.6×30 mm-3.5 μm); Mphase A 2% MeCN in 98% $H_2O$-10 mM $NH_4COOH$; Mphase B 98% MeCN in 2% $H_2O$-10 mM $NH_4COOH$; Flow: 1.8 ML/min; Time: 0; % A: 100; % B: 0; Time: 1.5; % A: 0; % B: 100; RT min: 1.868, wavelength: 220 nm.

5-(4-Fluoro-2-(4-fluorophenoxy)phenyl)-3-(methylcarbamoyl)benzofuran-5-yl)-2-methoxy-4-methylbenzoic acid. To a solution of methyl 5-(4-fluoro-2-(4-(4-fluorophenoxy)phenyl)-3-(methylcarbamoyl)benzofuran-5-yl)-2-methoxy-4-methylbenzoate (0.09 g, 0.16 mmol, 1.0 eq) in a 1:1 mixture of MeOH/THF at ambient temperature was added 1M NaOH (0.03 g, 0.75 mmol, 4.7 eq) solution, and the mixture then stirred at 60° C. for 3 h. The reaction mixture was concentrated, diluted with water, and acidified with 1.5 N HCl. The solid was filtered and washed with petroleum ether. Yield: 0.05 g (57.4%). $^1$H NMR (400 MHz, DMSO-$d_6$) δ 12.50 (s, 1H), 8.66 (q, J=4.8 Hz, 1H), 7.90-7.86 (m, 2H), 7.58-7.08 (m, 10H), 3.87 (s, 3H), 2.79 (d, J=4.8 Hz, 314), 2.21 (s, 3H). LCMS: (ES+) m/z=544.2 (M+H)$^+$; Column: Xbridge phe (4.6×30 mm-3.5 μm); Mphase A: 2% MeCN in 98% $H_2O$-10 mM $NH_4COOH$; Mphase B 98% MeCN in 2% $H_2O$-10 mM $NH_4COOH$; Flow: 1.8 mL/min; Time: 0; % A: 100; % B: 0; Time: 1.5; % A: 0; % B: 100; RT min: 1.529, wavelength: 220 nm.

4-Fluoro-2-(4-(4-fluorophenoxy)phenyl)-5-(4-methoxy-2-methyl-5-(1-(pyrimidin-2-yl)cyclopropylcarbamoyl)phenyl)-N-methylbenzofuran-3-carboxamide. To a mixture of 5-(4-fluoro-2-(4-fluorophenoxy)phenyl)-3-(methylcarbamoyl)benzofuran-5-yl)-2-methoxy-4-methylbenzoic acid (0.04 g, 0.073 mmol, 1.0 eq), 1-(pyrimidin-2-yl)cyclopropanamine HCl (0.020 g, 0.116 mmol, 1.6 eq) in DMF at 0° C. was added triethylamine (0.1 ml, 0.717 mmol, 9.8 eq) and PyBOP (0.06 g, 0.115 mmol, 1.58 eq). The reaction mixture was stirred at r.t. overnight, and then diluted with water and cooled to 0° C. The solid that precipitated out was filtered, and washed with water and dried under vacuum. The crude product was purified by preparative HPLC. Yield: 0.020 g (41.1%). $^1$H NMR (400 MHz, $CD_3OD$) δ 8.66 (d, J=4.8 Hz, 2H), 7.91-7.88 (m, 3H), 7.50 (d, J=8 Hz, 1H), 7.27-7.20 (m, 2H), 7.18-7.12 (m, 7H), 4.09 (s, 3H), 2.95 (s, 3H), 2.30 (s, 3H), 1.80 (m, 2H), 1.52 (m, 2H). $^{19}$F NMR (376.57 MHz, $CD_3OD$) δ −121.02, −122.94. (The $^{19}$F chemical shift was referenced to $CFCl_3$ at 0.0 ppm). LCMS: (ES+) m/z=661.2 (M+H)$^+$; Column: Ascentis ExpressC8(2.1×50 mm)-2.7 μm; Mphase A: 2% MeCN in 98% $H_2O$-10 mM $NH_4COOH$; Mphase B 98% MeCN in 2% $H_2O$-10 mM $NH_4COOH$; Flow: IML/min; Time: 0; % A: 100; % B: 0; Time: 1.5; % A: 0; % B: 100; RT min: 2.04, wavelength: 220 nm. HPLC Method: SUNFIRE C18 (4.6×150) mm, 3.5 micron; Buffer: 0.05% TFA in water pH 2.5; Mobile Phase A: Buffer:MeCN (95:5); Mobile Phase B: MeCN:Buffer (95:5); FLOW: 1 mL/min; Time: 0; B %: 10; Time: 25; B %: 100; Wavelength: 254 nm, RT min: 20.793; Wavelength: 220 nm, RT min: 20.793.

HPLC Method: XBridege phenyl (4.6×150) mm, 3.5 micron; Buffer: 0.05% TFA in water pH 2.5; Mobile Phase A: 0.05% TFA in water:MeCN (95:5); Mobile Phase B: 0.05% TFA in MeCN:water (95:5); FLOW: 1 ml/min; Time: 0; B %: 10; Time: 25; B %: 100; Wavelength: 254 nm, RT min: 18.878; Wavelength: 220 nm, RT min: 18.878. PREPARATIVE HPLC METHOD: Column: XTerra C18(250×4.6)5μ); Mobile Phase A: 20 mM AMMONIUM ACETATE in Water; Mobile Phase B: MeCN; FLOW: 1 ml/min; Time: 0; B %: 60; Time: 20; B %: 60; Time: 22; B %: 100; Time: 25; B %: 100; RT: 11.962 min.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

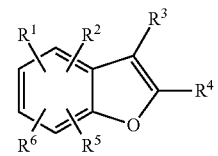

where:
$R^1$ is phenyl or pyridinyl and is substituted with 0-3 substituents selected from the group consisting of halo, alkyl, haloalkyl, hydroxyalkyl, alkoxyalkyl, alkoxy, hydroxyalkyloxy, and alkoxyalkyloxy, and is also substituted with 1 $CON(R^9)(R^{10})$ substituent;
$R^2$ is hydrogen, halo, or alkyl;
$R^3$ is $CONHCH_3$;
$R^4$ is phenyl that is para substituted with X—$Ar^1$;
$R^5$ and $R^6$ are independently hydrogen, alkyl, halo, $N(R^7)(R^8)$, or alkylsulfonyl;
$R^7$ and $R^8$ are independently hydrogen, alkyl, hydroxyalkyl, alkoxyalkyl, alkylsulfonyl, or alkylsulfonylalkyl; or $N(R^7)(R^8)$ taken together is azetidinyl, pyrrolidinyl, piperidinyl, or piperazinyl, and is substituted with 0-2 substituents selected from alkyl, hydroxyalkyl, or hydroxy;
$R^9$ is hydrogen;
$R^{10}$ is

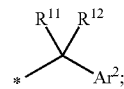

$R^{11}$ and $R^{12}$ are independently hydrogen, alkyl, hydroxyalkyl, or alkoxyalkyl;
or $R^{11}$ and $R^{12}$ taken together is ethylene, propylene, butylene, pentylene, or hexylene;
X is —O— or —NH—;
$Ar^1$ is phenyl or para-halophenyl; and
$Ar^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, or pyrimidinyl, and is substituted with 0-3 substituents selected from halo, alkyl, or dialkylamino;

or a pharmaceutically acceptable salt thereof.

2. A compound of claim 1 where $R^1$ is phenyl substituted with 0-3 substituents selected from the group consisting of halo, alkyl, hydroxyalkyl, alkoxyalkyl, alkoxy, or hydroxyalkyloxy, and is also substituted with 1 $CON(R^9)(R^{10})$ substituent;

$R^2$ is hydrogen or F;

$R^3$ is $CONHCH_3$ $R^4$ is phenyl that is para substituted with X—$Ar^1$;

$R^5$ and $R^6$ are hydrogen;

$R^{11}$ and $R^{12}$ are independently methyl or $R^{11}$ and $R^{12}$ taken together is ethylene or propylene;

X is —O—;

$Ar^1$ is para-fluorophenyl; and $Ar^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, pyrimidinyl, and is substituted with 0-3 substituents selected from halo or alkyl;

or a pharmaceutically acceptable salt thereof.

3. A compound of claim 2 where $R^1$ is phenyl substituted with 0-2 substituents selected from the group consisting of alkyl and alkoxy, and is also substituted with 1 $CON(R^9)(R^{10})$ substituent; $R^2$ is F; $R^3$ is $CONHCH_3$; $R^4$ is phenyl that is para substituted with X—$Ar^1$; $R^5$ and $R^6$ are hydrogen; $R^{11}$ and $R^{12}$ taken together is ethylene; X is —O—; $Ar^1$ is para-fluorophenyl; and $Ar^2$ is pyrimidinyl; or a pharmaceutically acceptable salt thereof.

4. The compound of claim 3

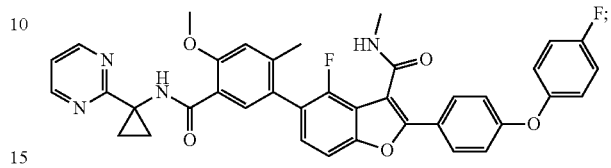

or a pharmaceutically acceptable salt thereof.

5. A composition comprising a compound of claim 1 or a pharmaceutically acceptable salt thereof and a pharmaceutically acceptable carrier.

6. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

| | | |
|---|---|---|
| PATENT NO. | : 8,445,497 B2 | Page 1 of 1 |
| APPLICATION NO. | : 13/167356 | |
| DATED | : May 21, 2013 | |
| INVENTOR(S) | : Kap-Sun Yeung et al. | |

It is certified that error appears in the above-identified patent and that said Letters Patent is hereby corrected as shown below:

In the Claims:

Claim 2:

Column 17, line 5, change "where" to -- where: --.

Column 17, line 11, change "CONHCH$_3$" to -- CONHCH$_3$; --.

Signed and Sealed this
Twenty-ninth Day of April, 2014

Michelle K. Lee
*Deputy Director of the United States Patent and Trademark Office*